US00PP10024P

United States Patent [19]

Lemon

[11] Patent Number: Plant 10,024

[45] Date of Patent: Sep. 9, 1997

[54] GERANIUM PLANT NAMED 'JENNIFER'

[75] Inventor: David Lemon, Lompoc, Calif.

[73] Assignee: John Bodger and Sons Company, South El Monte, Calif.

[21] Appl. No.: 571,202

[22] Filed: Dec. 12, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 6,014 9/1987 Kirmann ..... Plt./87.12

P.P. 6,018 9/1987 Kirmann ..... Plt./87.12

P.P. 6,027 9/1987 Kirmann ..... Plt./87.12

*Primary Examiner*—Howard J. Locker

[57] ABSTRACT

The cultivar is characterized by its bright clear white colored flower. Its improved rooting ability and prolific flowering provide excellent characteristics not found in other Regal varieties. The plant flowers over a longer period of time than do other Regal varieties and is slow to shatter.

1 Drawing Sheet

BACKGROUND OF THE NEW PLANT

The present invention comprises a new and distinct cultivar of *Pelargonium×domesticum* known by the varietal name Jennifer (Oglevee No. 664, Bodger No. 10PD 13-7). The new variety was discovered in a selective breeding program by David Lemon at Bodger Seeds, Ltd., Lompoc, Calif. The new variety is a selection from the crossing of White Glory (unpatented)×Bodger No. 8 PD 28-4, which is a cross of White Champion (unpatented)×Anastasia (unpatented). White Glory has large, pure white flowers and light green leaves and a tall growth habit. White Champion also has pure white flowers and is relatively difficult to propagate. Anastasia is a relatively late flowering variety. Jennifer, on the other hand, has large white flowers with magenta purple lines accenting the center of the flowers, medium green leaves, is relatively easy to propagate, and is an early flowering variety.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 150–200 parts per million of nitrogen and potassium has a response time of fourteen weeks from the rooted cutting to a flowering plant in a six inch pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings potted on Nov. 4, 1994 which flowered on Feb. 10, 1995 under full light and greenhouse, and colorings were taken indoors under 200–220 foot candles of fluorescent cool white light using R.H.S. Colour Chart of The Royal Horticultural Society of London.

THE PLANT

Classification:
- *Botanical.*—*Pelargonium×domesticum.*

Form: Upright mound shaped habit.
- *Height.*—22.0–24.0 cm above the media surface.
- *Growth.*—Fast rooting; prolific flowering.
- *Strength.*—Free standing.

Foliage: Stalked leaf attachment.

Leaves:
- *Size.*—8.0–11.0 cm across; fully expanded leaf.
- *Shape.*—Depressed ovate; truncate base.
- *Margin.*—Serrately lobed.
- *Texture.*—Slightly pubescent; leathery.
- *Color.*—Top: Green Group 137C; Zone: Not present. Bottom: Yellow/Green Group 147B.
- *Ribs and veins.*—Palmate venation; Color: Yellow/Green group 147C.

Petioles:
- *Length.*—4.0–7.0 cm.
- *Color.*—Yellow/green group 146B.

Stem:
- *Color.*—Yellow/green group 146B.
- *Internodes.*—1.5–3.5 cm in length.

THE BUD

Shape: Elliptical.
Size: 2.5–3.0 cm across.

INFLORESCENCE

Blooming habit: Many large opening into full flower head.
Size: 9.5–12.0 cm across.
Borne: Umbel; florets on pedicel; pedicel on peduncle.
Number: About 29 inflorescences per plant.

Florets:
- *Closed.*—Bud size: 1.5–2.0 cm in length, 0.5–1.0 cm in width; elliptical; bud showing no color.
- *Open.*—Form—Cupped. Color—Top: White Group 155D with a slight veining of Red/Purple Group 67C on the upper two petals; Bottom petals: White Group 155D. Petals—5–6 in number; single; not united; margin entire. Size—5.0–6.0 cm. Texture and apperance—Satiny; smooth; appearance from a distance is a bright clear white flower and medium green foliage.

Petaloids:

Quantity.—None.

Pedicel:

*Length.*—1.5–2.5 cm.

*Color.*—Yellow/Green Group 146C.

Peduncle:

*Length.*—5.0–6.5 cm.

Color.—Yellow/Green Group 146B.

Persistence:

*Disease resistance.*—Not known.

*Lasting quality.*—Continuous blooming; slow to shatter.

REPRODUCTIVE ORGANS

Stamens:

*Anthers.*—3.0–4.0 mm.

*Filaments.*—Length: 2.0—2.5 cm; Color: White group 155D.

*Pollen.*—Golden Brown.

Pistils:

*Number.*—One.

*Length.*—2.0–2.5 cm.

*Stigma.*—Five parted; Color: Red/Purple Group 60C.

*Style.*—Length: 1.0–1.5 cm; Color: Red/Purple Group 60C.

Ovaries: Pubescent; Color: light green.

Fruit: None observed.

GENERAL CHARACTERISTICS

Jennifer is a new bright clear white variety of geranium which is an improvement over the Regal geranium class. It improves on the current variety Mary (U.S. Plant Pat. No. 6,027) by rooting more easily and faster. The plant habit is shorter and more controlled, and the foliage color is a richer green and does not yellow with age as does the variety Mary. The plant flowers over a long period of time and is slower to shatter. Given all these positive properties, this variety should please both the grower and the gardener.

I claim:

1. A new and distinct variety of Geranium plant, substantially as shown and described.

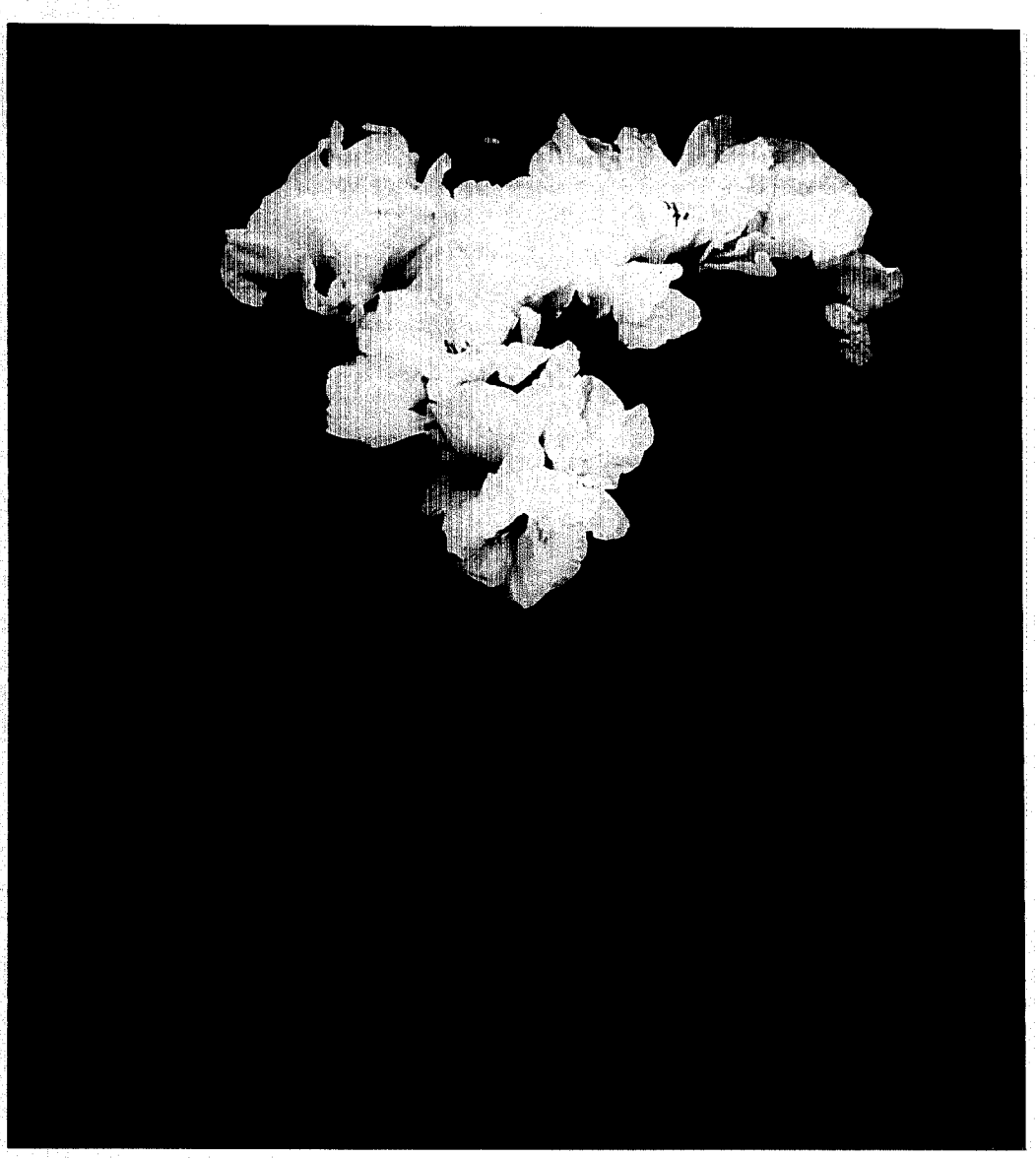

* * * * *